(12) United States Patent
Spychalski

(10) Patent No.: US 6,418,792 B1
(45) Date of Patent: Jul. 16, 2002

(54) PRESSURE COMPENSATED TRANSDUCER

(76) Inventor: Stephen Edward Spychalski, 11501 Coleman Rd., Gulfport, MS (US) 39503

( * ) Notice: Subject to any disclaimer, the term of this patent is extended or adjusted under 35 U.S.C. 154(b) by 0 days.

(21) Appl. No.: 09/405,194

(22) Filed: Sep. 24, 1999

(51) Int. Cl.[7] .......................... G01N 29/00; H04R 17/00
(52) U.S. Cl. ...................... 73/649; 73/54.16; 367/167
(58) Field of Search .................. 73/649, 570, 152.27, 73/54.16; 381/189; 367/167, 172

(56) References Cited

U.S. PATENT DOCUMENTS

| | | | |
|---|---|---|---|
| 3,995,501 A | * 12/1976 | Wiley | 73/560 |
| 4,074,224 A | 2/1978 | Laurent | 367/166 |
| 4,336,639 A | 6/1982 | Berglund | 310/337 |
| 4,345,467 A | * 8/1982 | Carlson | 73/309 |
| 4,669,309 A | * 6/1987 | Cornelius | 73/299 |
| 4,996,675 A | 2/1991 | Beauducel | 367/162 |
| 5,140,560 A | * 8/1992 | Percy | 367/174 |
| 5,191,559 A | * 3/1993 | Kahn et al. | 367/157 |
| 5,196,755 A | 3/1993 | Shields | 310/322 |
| 5,531,113 A | * 7/1996 | Jamison | 73/167 |
| 5,948,993 A | * 9/1999 | Ting et al. | 73/777 |
| 6,354,146 B1 | * 3/2002 | Birchak et al. | 73/61.79 |

OTHER PUBLICATIONS

O'Neil, "Hydrophone Development at Hudson Laboratories", TR 108, Sep. 24, 1963, pp 16, USA.

* cited by examiner

Primary Examiner—Hezron Williams
Assistant Examiner—Jacques Saint-Surin
(74) Attorney, Agent, or Firm—George E. Stanford, Jr.

(57) ABSTRACT

A pressure compensated sound transducer is provided wherein compensation and equalization of static ambient pressure variations occurring on the faces of at least one piezoelectric element is achieved by a mensural compensating duct communicating compensating fluid between two reservoirs, each located on an opposite face of a piezoelectric element. One reservoir is formed in the void of the support housing containing at least one piezoelectric element; the remaining reservoir is formed in the void between the housing and a sealed impermeable, compliant boot. The sealed boot prevents contamination of the compensating fluid from the external environment and loss of the compensating fluid to the outside environment.

20 Claims, 5 Drawing Sheets

PRESSURE COMPENSATED TRANSDUCER

BACKGROUND

1. Field of the Invention

The present invention concerns generally a sound transducer for either receiving or transmitting sound, including subsonic, audible, and ultrasonic sound. In particular, the present invention is directed to a pressure-compensated sound transducer incorporating at least one piezoelectric element fixed to a concomitant flexural metal plate for use in ambient environments wherein the pressure is greater than that normally expected at the earth's surface, especially in high-pressure hydrostatic or geostatic operating environments. For example, utilized either as a single element or combined in various two and three dimensional arrays, the present invention provides ambient pressure-compensation means for sound transducer systems used in either maritime or borehole environments by the petroleum industry for petroleum resource exploration, exploitation and monitoring.

2. Description of Related Art

The myriad benefits accrued from the sound transducer process of converting between mechanical and electrical energy has provided the impetus for many inventions, including the incorporation of dual piezoelectric elements in a single transducer assembly to gain certain signal conditioning advantages.

Figure 1:
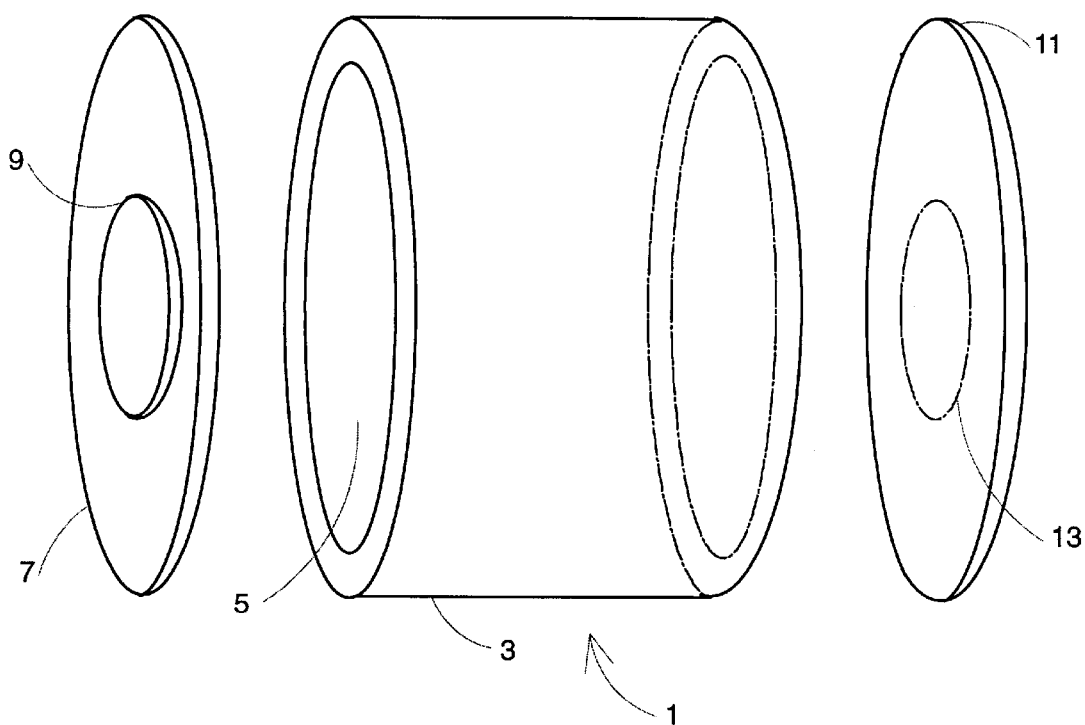

For example, FIG. 1, exploded perspective view, exemplifies a prior art uncompensated dual element piezoelectric transducer assembly. Uncompensated transducer assembly 1 comprises a ring support 3 that maintains a first flexural metal disk 7 and a second flexural disk 11 in a fixed relation to each other. First flexural disk 7 provides propagation medium coupling to first piezoelectric element 9 affixed thereto. In like manner, second piezoelectric element 13 is fixed to second flexural disk 11, the disk providing mechanical coupling between the medium and the piezoelectric element. Electrically connected in either series or parallel configurations, the dual piezoelectric assembly provides numerous signal-conditioning advantages.

Typically, transducer assembly 1 has been hermetically sealed to keep out foreign fluids and substances, and ring support void 5 is filled with a gas. Unfortunately, this manufacturing process created problems whenever the transducer was operated in ambient pressure environments considerably above normal atmospheric pressure. Numerous schemes have been employed to compensate for this problem. Some remedies entail the use of absorbent substances in the void of the transducer ring support. For example, filling the interior of the ring support housing with an absorbent material saturated with a fluid has been used in conjunction with opening the ring interior to the surrounding medium. U.S. Pat. No. 4,996,675 "SIGNAL SENSOR INSENSITIVE TO STATIC PRESSURE VARIATIONS" is incorporated herein by reference for purposes of indicating the background of the present invention or illustrating the mature state of the art for use of an absorbent material to compensate for the effects of ambient static pressure on the sensor.

The continuing quest for new petroleum resources has led exploration teams from relatively benign sites to sites where the environment is more extreme, and perhaps hazardous. This geographic shift has heightened the desire for simple, reliable, economical sound transducers, employing a minimum of parts and no moving parts, which can be operated in high ambient pressure environments.

SUMMARY

It is an object of the present invention to provide a pressure compensated sound transducer incorporating at least one piezoelectric element and concomitant flexural metal plate, wherein the pressure compensation means is at least one mensurational duct, the duct having predetermined duct mensural parameters derived from calculations, for communicating pressure compensating fluid between an inner reservoir and an outer reservoir, each piezoelectric element, each reservoir and the mensurational duct enclosed within a sealed, protective, compliant boot. It is an additional object of the present invention to provide a pressure compensated sound transducer incorporating at least one piezoelectric element and concomitant flexural metal disk, and at least one mensurational duct, wherein the transducer may be employed as either a sound receiving device, for example, a hydrophone, or a sound transmitting device, for example, a sound projector, and wherein the pressure compensation means is both passive and simple. It is a further objective of the present invention to provide a pressure compensated sound transducer incorporating at least one piezoelectric element and concomitant flexural metal disk, and at least one mensurational duct, wherein the pressure compensated sound transducer may be employed singly or assembled into an array, the array being a line array, a planar array, a volumetric array, or any combination thereof.

BRIEF DESCRIPTION OF THE DRAWING(S)

FIG. 1 is an exploded perspective view of an exemplary prior art dual piezoelectric element transducer.

Figure 2:
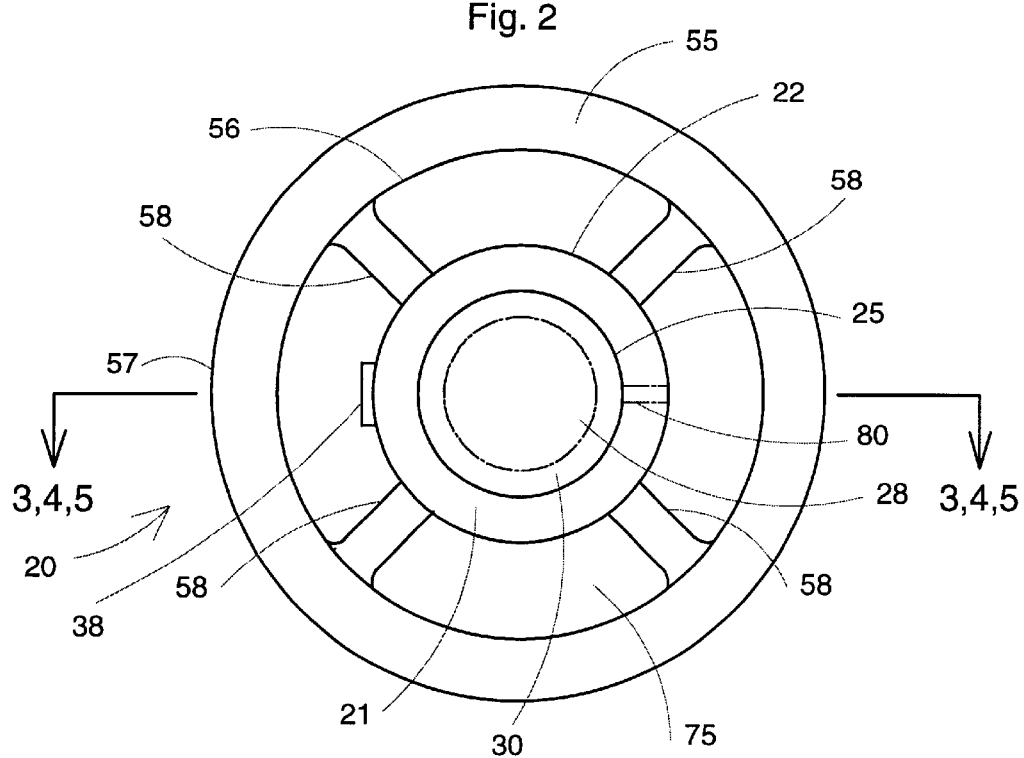

FIG. 2 is an exemplary end view of an embodiment of the present invention with the end cap and sealing band removed, illustrating the protective compliant boot, viewed toward the boot singular opening, and four molded compliant ribs for receiving the support housing and maintaining position of the support housing within the inner wall of the boot. Lines 3—3, 4—4, and 5—5 define three side sectional views to further expedite description of an embodiment of the present invention. Electrical circuitry connecting the two piezoelectric elements to each other and to a sound signal conditioning system is well known to those practicing the art; to provide maximum clarity to the illustration, this connecting circuitry is not shown.

Figure 3:
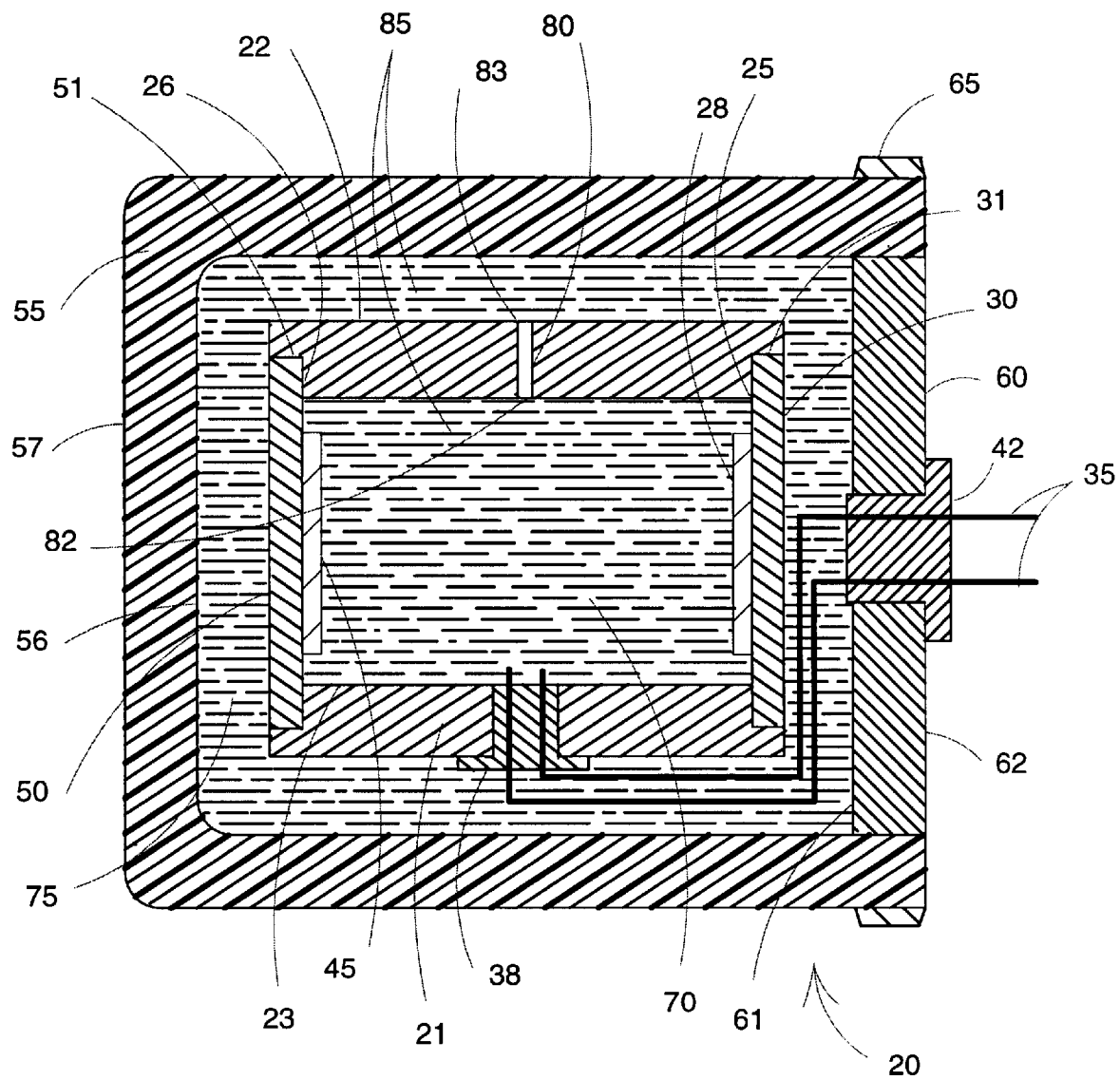

FIG. 3 is an exemplary sectional side view of an embodiment of the present invention illustrating the pressure-compensated transducer incorporating two piezoelectric elements and their concomitant flexural metal disks. This exemplary sectional view reveals the outer reservoir, defined by the void formed by the inner cap surface, the inner wall of the boot, and the outer surface of the support housing. In this view, the inner reservoir is also revealed, defined by the void formed by the inner surface of the support housing and the placement of each of the piezoelectric elements and their concomitant flexural metal plates placed thereon. This sectional view is filled with pressure compensating fluid to emphasize the location and shape of the inner and outer reservoirs, and also to show the pressure-compensating mensurational duct with outer and inner orifices providing communicating fluid flow between the outer reservoir and the inner reservoir. This sectional view showing a fluid-filled outer reservoir obscures the view of the molded ribs. Electrical circuitry connecting the two piezoelectric elements to each other and to a sound signal conditioning system is well known to those practicing the art; to provide maximum clarity to the illustration, this connecting circuitry is not shown.

Figure 4:
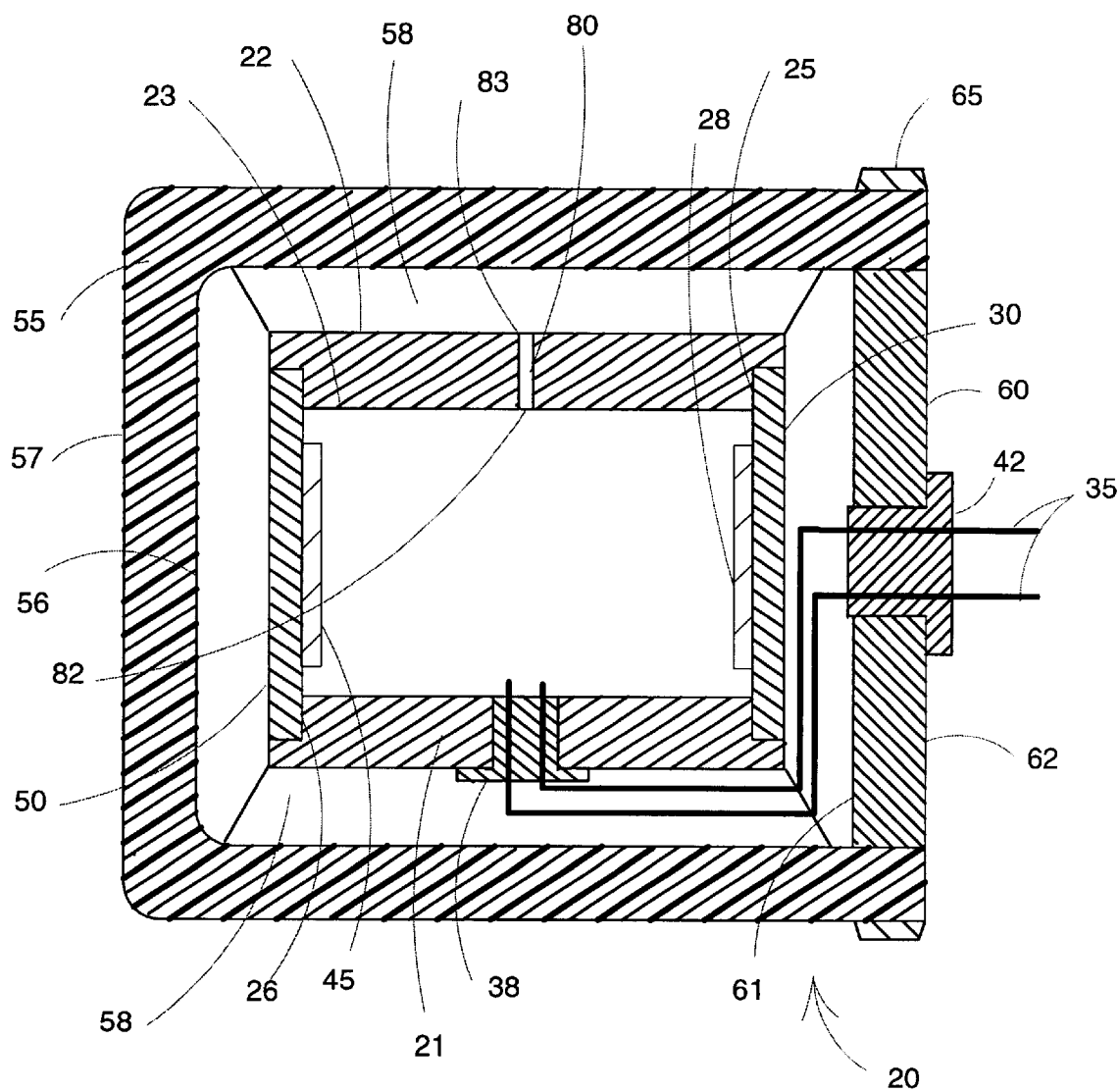

FIG. 4 is an exemplary sectional side view of an embodiment of the present invention illustrating the pressure-compensated transducer incorporating two piezoelectric elements and their concomitant flexural metal disks. This sectional view is empty of any pressure compensating fluid to emphasize the location and shape of the boot ribs that receive and maintain position of the support housing within the compliant boot. Electrical circuitry connecting the two piezoelectric elements to each other and to a sound signal conditioning system is well known to those practicing the art; to provide maximum clarity to the illustration, this connecting circuitry is not shown.

Figure 5:
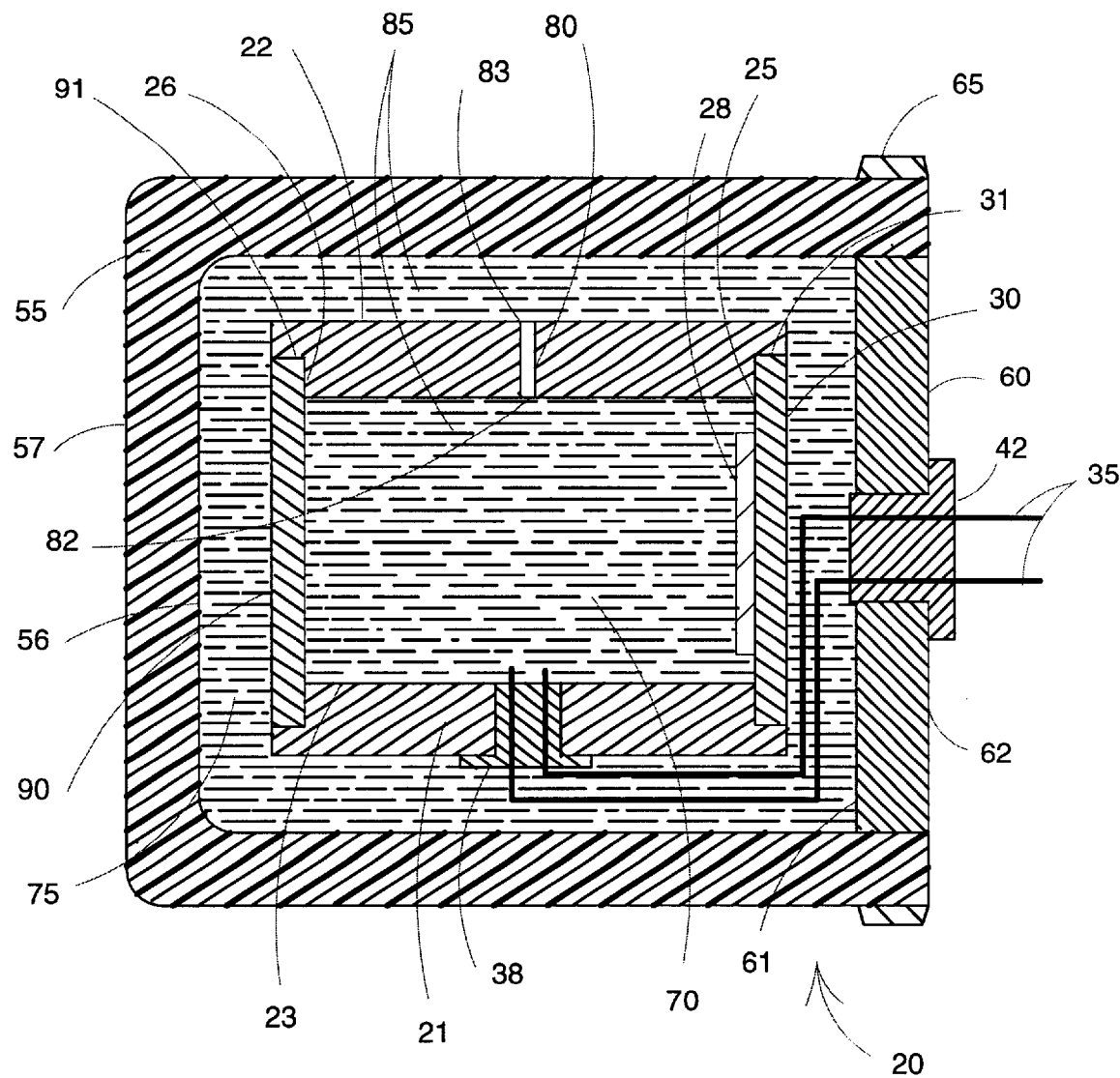

FIG. 5 is an exemplary sectional side view of an alternative embodiment of the present invention illustrating the pressure-compensated transducer incorporating a single piezoelectric element and a concomitant flexural metal disk, the second element and disk being replaced with a rigid, impermeable disk. This sectional view is filled with pressure compensating fluid to emphasize the location and shape of the inner and outer reservoirs, and also to show the pressure-compensating mensurational duct providing communicating fluid flow between the outer reservoir and the inner reservoir. Electrical circuitry connecting the single piezoelectric element to a sound signal conditioning system is well known to those practicing the art; to provide maximum clarity to the illustration, this connecting circuitry is not shown.

Figure 6:
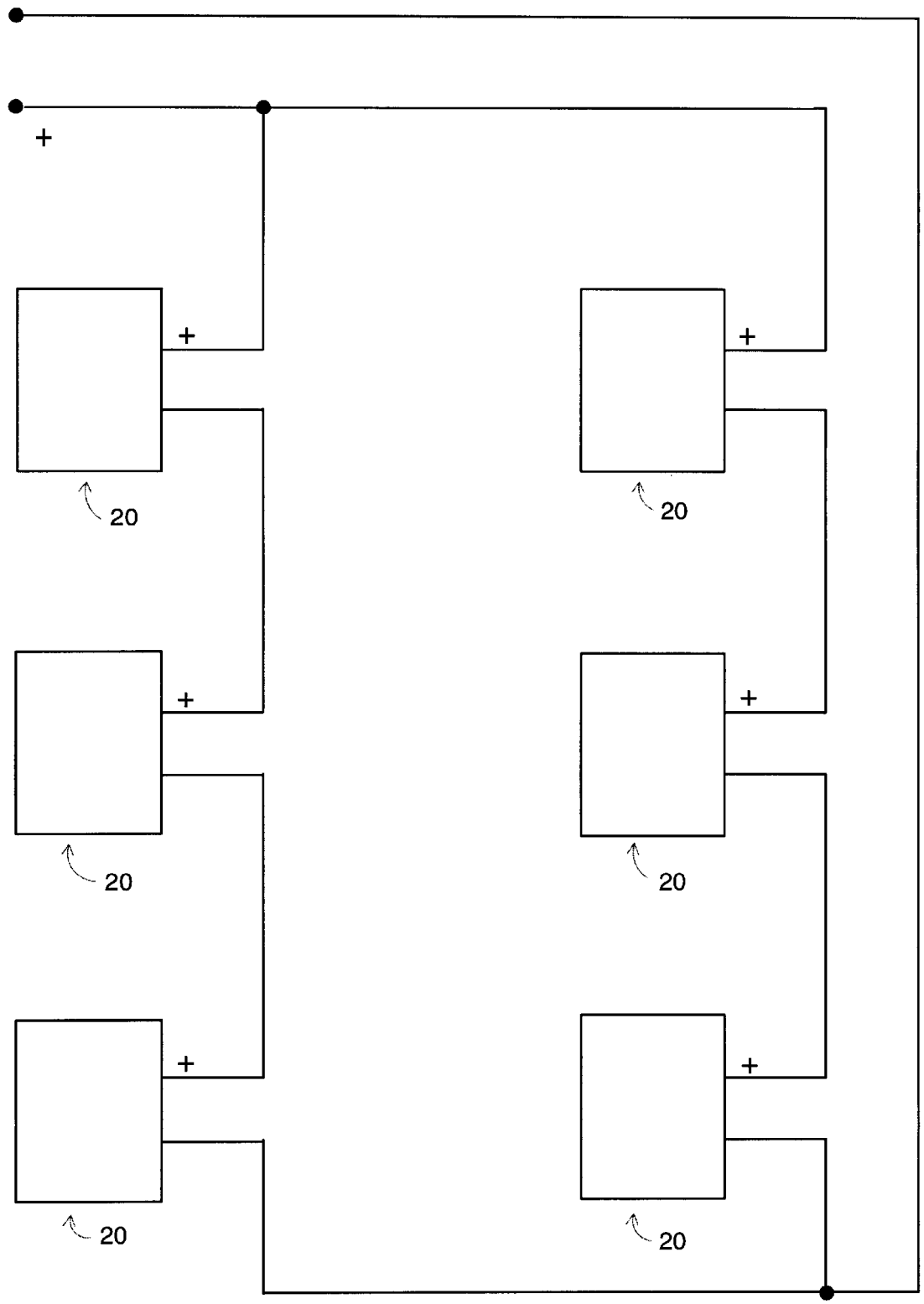

FIG. 6 is an exemplary block diagram of an alternative array embodiment of the present invention illustrating but one of a myriad possible combinations for connecting a replicated plurality of the present invention into a sound array, such as a line array, a planar array, or a volumetric array. A sound signal conditioning system, for transmitting or receiving a sound signal, normally connected to such an array embodiment is not shown.

DESCRIPTION OF THE PREFERRED EMBODIMENT

FIG. 2 illustrates an exemplary end view of the general structure of the preferred embodiment of the present invention. In this view of pressure-compensated transducer 20, end cap 60 and sealing band 65 (see FIG. 3) have been removed to reveal components normally totally enclosed within protective molded compliant impermeable boot 55. Protective boot 55 is generally a hollow cylinder with one end closed and a singular opening in the opposing end. The singular opening is capable of being sealed by receiving a sealing end cap 60 (see FIG. 3). Boot 55 is molded and fabricated from an impermeable compliant material such as rubber, plastic, or the like. In addition to the singular opening, boot 55 has an boot inner wall 56, an boot outer wall 57, and a plurality of molded boot ribs 58 molded into wall 56. The lengthwise axis of each of the ribs 58 is generally parallel to the lengthwise axis of boot 55. The diameter of the void defined by inner wall 56 and the width, height, and length of ribs 58 are determined such as to receive and securely maintain position of hollow, cylindrical, impermeable housing 21 within inner wall 56. The void within boot 55, between the outer surface 22 of housing 21 and boot inner wall 56, totally surrounding housing 21, defines outer reservoir 75. The extent of the void is limited by inner cap surface 61 of end cap 60 (see FIG. 3).

The view of FIG. 2 looks into the open end of boot 55, revealing a first flexural metal plate 30, affixed to housing 21. Beneath plate 30, illustrated with hidden lines, is an associated first piezoelectric element 28, securely affixed to plate 30 by means of an electrically conducting bonding agent. Plate 30 and piezoelectric element 28 are commercially available and techniques for their assembly are well know to those skilled in the art.

The open-end view of FIG. 2 additionally reveals pressure-compensating mensurational duct 80, shown by hidden lines, providing communication between outer reservoir 75 and the interior void of housing 21. Pressure-compensating mensurational duct 80 is defined hereby to be a duct whose mensural parameters have been calculated and determined prior to fabrication thereof. With the exception of duct 80, upon completion of manufacture the interior void of support housing 21 is sealed and impermeable. First piezoelectric element 28 is positioned within the interior void of housing 21. First impermeable feedthrough electrical connector 38 provides means for electrical connectivity between piezoelectric element 28 and associated sound signal conditioning systems (not shown and not claimed in the present invention) external to housing 21. Feedthrough 38 is readily and commercially available.

The preferred embodiment of the present invention is further described in exemplary FIG. 3, defined by section line 3—3 of FIG. 2. FIG. 3 is a side sectional view of a complete transducer 20, with end cap 60 inserted into the singular opening of protective boot 55 and securely fastened thereto by means of sealing band 65, effectively sealing boot 55 from external environmental effects, such as foreign fluids and substances. To clarify description of the present invention, all voids within boot 55 are completely filled with a requisite pressure-compensating fluid 85. The fluid 85 obscures viewing ribs 58 (not shown in FIG. 3).

The preferred embodiment of the present invention is further described in FIG. 4, defined by section line 4—4 of FIG. 2. This view is devoid of pressure-compensating fluid 85 to more clearly describe the plurality of molded compliant boot ribs 58. Boot 55 and ribs 58 are simultaneously molded from the same compliant material.

The preferred embodiment of the present invention, FIG. 3, provides a pressure compensated piezoelectric transducer 20 incorporating two piezoelectric elements. First piezoelectric element 28 is affixed to concomitant first flexural metal plate 30 with an electrically conducting bonding agent, and second piezoelectric element 45 is similarly affixed to concomitant second flexural metal plate 50 with an electrically conducting bonding agent, as is commonly practiced in the art. First plate 30 has a first peripheral edge 31; similarly, second plate 50 has a second peripheral edge 51. The piezoelectric elements may be piezoelectric ceramic wafers, piezoelectric polymer film, such as poly vinylidene fluoride (PVDF), or like piezoelectric materials. Both piezoelectric elements and flexural metal plates are commercially available.

Support housing 21 is tubular, rigid, impermeable and preferably fabricated from an electrically conductive material. Housing 21 features an outer surface 22, an inner surface 23, a first rim 25 encompassing an open end of housing 21 and a second rim 26 encompassing the opposing open end of housing 21. First peripheral edge 31 of plate 30 is affixed to rim 25 of housing 21 with an electrically conducting bonding agent. In like manner, second peripheral edge 51 of plate 50 is affixed to rim 26 of housing 21, the aggregated fabrication of plates 30 and 50, and inner surface 23 defining inner reservoir 70 in the void of housing 21.

Piezoelectric elements 28 and 45 may be electrically connected and configured in various series and parallel circuits as a piezoelectric element configuration circuit (not shown and not claimed in the present invention) using techniques widely known to those skilled in the art.

Penetrating housing 21 is first impermeable feed-through electrical connector 38, for connecting the piezoelectric element configuration circuit, via electrical connection leads 35, to a sound signal conditioning system comprising receiving or transmitting circuitry (not shown). Such signal conditioning systems and circuits are well known to those practicing the art and are not claimed in the present invention. An alternative to first feed-through connector 38 is piercing housing 21, feeding leads 35 through the resultant aperture, and finally sealing the aperture with an appropriate sealing compound, such as plastic resin, silicone putty, or synthetic rubber.

The nexus of pressure compensation for maritime and geophysical sound transducers is the relief of the static stress differential pressure across the opposite surfaces of a thin piezoelectric element. It can be seen from FIG. 3, that one surface of each of the two piezoelectric elements, 28 and 45, faces inner reservoir 70. Conversely, the opposite face of each of the two piezoelectric elements, 28 and 45 is bonded to a concomitant flexural plate, 30 and 50, respectively, which has a surface exposed to outer reservoir 75. Thus, any static stress differential pressure occurring across the opposite faces of each of the two piezoelectric elements, 28 and 45, will be manifested as a difference in static pressure between the fluid in the inner reservoir 70 and the fluid in the outer reservoir 75.

Pressure compensation between inner reservoir 70 and outer reservoir 75 is effected by piercing the impermeable structure of housing 21 with pressure compensating mensurational duct 80, having inner orifice 82 and outer orifice 83. The operational effectiveness of the pressure compensation technique embodied in the present invention is dependant upon the mensural parameters of duct 80, the volume of inner reservoir 70 and the viscosity and bulk modulus of pressure compensating fluid 85.

The mensural parameters of mensurational duct 80 include length and diameter. Judicious selection of these parameters will determine the effective operating sound bandwidth of the present invention. In the preferred embodiment, the mensural parameters of mensurational duct 80 are derived from calculations developed in "Hydrophone Development at Hudson Laboratories", E. T. O'Neil, Columbia University Hudson Labs, Technical Report No. 108, 1963. Technical Report No. 108 is incorporated by reference herein to demonstrate the state of the art in the calculated determination of mensural parameters of pressure-compensating ducts, conduits, and tubes. The mathematical expressions developed in O'Neil's report are derived from the Hagen-Poiseuille law for laminar flow in circular pipes. O'Neil's derivation determines $f_0$ as the frequency at which the sound power is one-half (−3 dB) that of the sound power in the desired sound frequency band, i.e. the operating sound bandwidth of the transducer. $f_0 = \frac{1}{2\pi T}$ where T is the time constant of the pressure compensating system, from which O'Neil derives, $$f_0 = \frac{D^4 B_e}{256 \, \mu L \, V_r}$$

where,

D=diameter of pressure compensating mensurational duct 80 (inches)

L=length of pressure compensating mensurational duct 80 (inches)

$B_e$=bulk modulus of pressure compensating fluid 85 (psi)

$V_r$=volume of inner reservoir 70 (inches$^3$)

$\mu$=dynamic viscosity of pressure compensating fluid 85 (lb-sec/inch$^2$)

Employment of the present invention includes operational use in adverse and hostile environments, such as, in geophysical boreholes, in the ocean depths, or buried beneath the seafloor. To protect housing 21 from potentially risky environments, boot 55, having boot inner wall 56 and boot outer wall 57, is sealed with endcap 60, secured to boot 55 with sealing band 65.

Endcap 65 features a high-pressure electrical feed-through connector 42 for passing a plurality of electrical connection leads 35 through the sealed boot 55, connecting the piezoelectric element configuration circuit within housing 21 to an external sound signal conditioning system for either receiving or transmitting a sound signal. Feedthrough 42 is readily and commercially available.

Assembly of pressure compensated piezoelectric transducer 20 entails submerging all components beneath the surface of a pressure compensating fluid 85. This technique is employed to purge any gas bubbles entrained within transducer 20. Preferably, fluid 85 is a commercially available viscous, non-conducting fluid, such as castor oil (DB grade) or DC 200 silicone fluid, or the like. The key physical properties of fluid 85 affecting the choice of the pressure compensating fluid include bulk modulus and viscosity. Another important parameter influencing the choice of fluid 85 is the temperature range expected to be encountered in the operating environment. Upon purging all gases and foreign substances from within boot 55 and insuring both inner reservoir 70 and outer reservoir 75 are completely filled with compensating fluid 85, housing 21 is received by and maintained in position by boot ribs 58. Next, endcap 60 is inserted into boot 55, snugly fitting against boot inner wall 56. Sealing of boot 55 is completed by means of sealing band 65. Such sealing prevents any environmental fluids or substances from contaminating the volume within inner wall 56 and additionally prevents any compensating fluid 85 from escaping into the external environment.

During assembly of pressure compensated transducer 20, care is taken when inserting support housing 21 into boot 55 to insure outer orifice 83 is not obstructed or otherwise restricted by boot ribs 58.

An alternative embodiment of the present invention is described in FIG. 5, defined by section line 5—5 of FIG. 2. FIG. 5 illustrates a single piezoelectric element embodiment of the present invention, similar to FIG. 2, wherein rigid plate 90 is substituted for second piezoelectric element 45 and concomitant flexural disk 50.

Pressure compensated transducer 20 can be utilized as a solitary source, for example, a sound projector, or a solitary receiver of sound wave propagation, for example, a hydrophone. Alternatively, a plurality of devices, each such device transducer 20, can be configured and assembled into various line, surface, and volumetric arrays, or combinations thereof. FIG. 6 illustrates but one of a myriad possible series-parallel combinations of a plurality assemblage of the present invention.

Although only a few exemplary embodiments of the invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-functions clauses are intended to cover the structures described herein as performing the recited functions and not only structural equivalents but also equivalent structures.

What is claimed is:

1. A pressure compensated transducer for transmitting and receiving sound, said transducer comprising:

a rigid, impermeable, support housing, said housing having an outer surface, said outer surface having at least one opening penetrating said housing, said outer surface otherwise defining a closed surface, said housing having an inner surface, each of said at least one opening having a rim bordering thereto, said housing having a first connecting means for a plurality of electrically conducting leads penetrating thereinto;

a pressure compensating mensurational duct, having an inner orifice and an outer orifice, said duct piercing said housing, said inner orifice abutting said inner surface of said housing and said outer orifice abutting said outer surface of said housing, said mensurational duct having mensural parameters calculated and determined prior to fabrication thereof;

at least one piezoelectric element, each said element corresponding in number to each of said at least one opening, each said element affixed to a concomitant flexural metal plate by means of an electrically conductive bonding agent, each said plate having a peripheral edge, each said peripheral edge of each said plate impermeably affixed and sealed to corresponding each said rim of each of said at least one opening of said housing, each of said at least one piezoelectric element electrically connected to each other in a piezoelectric element configuration circuit, the piezoelectric element configuration circuit electrically connected to a plurality of electrically conducting leads, said conducting leads connecting to said first connecting means and extending therefrom, for subsequently connecting the piezoelectric element configuration circuit to a sound signal conditioning system;

a protective boot, for retaining and protecting a pressure compensation fluid, said boot fabricated from a compliant impermeable material, said boot having a boot outer wall, a boot inner wall, and a singular opening thereinto, said boot inner wall having a plurality of boot ribs molded thereinto, said boot and said ribs receiving said housing and securely maintaining position of said housing within said boot, said boot further having an impermeable, rigid end cap, having an inner cap surface and an outer cap surface, said cap having a second electrical connecting means penetrating thereinto, said second connecting means receiving said plurality of electrical conducting leads connected to said first connecting means and extending therefrom, said second connecting means having said leads extending therefrom, said connecting leads further connected from said second connecting means to the sound signal conditioning system, said end cap received into and affixed against said inner wall of said boot with a sealing band, for preventing contamination of the compensating fluid from the external environment and preventing loss of the compensating fluid to the external environment;

an inner reservoir, defined by the void bounded by said inner surface of said housing and each said rim of each said opening of said housing; and an outer reservoir, enveloping said housing, defined by the void between said outer surface of said housing, said boot inner wall of said boot, and said inner cap surface of said end cap, said inner reservoir and said outer reservoir completely filled with the pressure compensating fluid, said inner orifice of said mensurational duct proximate to said inner reservoir and said outer orifice of said duct proximate to said outer reservoir, for communicating flow of the pressure compensating fluid between said outer reservoir and said inner reservoir, for providing pressure compensation and equalization of ambient pressure variations on each surface of each of said at least one piezoelectric element.

2. A pressure compensated transducer for transmitting and receiving sound as recited in claim 1, wherein each said at least one piezoelectric element and concomitant flexural metal plate is shaped as a disk, each corresponding said opening of said housing is circular, each said opening having a rim for correspondingly receiving each said plate thereto.

3. A pressure compensated transducer for transmitting and receiving sound as recited in claim 2, wherein said at least one opening penetrating said housing comprises one opening, said one opening having an opening rim bordering said one opening, said at least one piezoelectric element comprises one piezoelectric disk element, said one element affixed to a concomitant flexural metal disk by means of an electrically conducting bonding agent, said plate having a peripheral edge, said peripheral edge impermeably affixed and sealed to said opening rim of said opening of said housing.

4. A pressure compensated transducer for transmitting and receiving sound, as recited in claim 2, wherein said at least one opening of said housing comprises a first opening having a first rim bordering thereto and a second opening having a second rim bordering thereto; said at least one piezoelectric element comprises a first piezoelectric element, affixed to a concomitant first flexural metal plate by means of an electrically conductive bonding agent, said first plate having a first peripheral edge, said first peripheral edge impermeably affixed and sealed to said first rim of said housing; said at least one piezoelectric element further comprises a second piezoelectric element, affixed to a concomitant second flexural metal plate by means of an electrically conductive bonding agent, said second plate having a second peripheral edge, said second peripheral edge impermeably affixed and sealed to said second rim of said housing, said first piezoelectric element and said second piezoelectric element electrically connected to each other in the piezoelectric element configuration circuit, the piezoelectric element configuration circuit electrically connected to said plurality of electrically conducting leads, said conducting leads connecting to said first connecting means and extending therefrom, for subsequently connecting the piezoelectric element configuration circuit to a sound signal conditioning system.

5. A pressure compensated transducer for transmitting and receiving sound, as recited in claim 4, wherein said housing is tubular, having a first open end corresponding to a first opening and a second open end corresponding to a second opening, said open ends opposing each other.

6. A pressure compensated transducer for transmitting and receiving sound, as recited in claim 5, wherein said first connecting means for a plurality of electrically conducting leads comprises a first impermeable feedthrough electrical connector penetrating said housing thereinto.

7. A pressure compensated transducer for transmitting and receiving sound, as recited in claim 6, wherein said second connecting means for a plurality of electrically conducting leads comprises a second impermeable feedthrough electrical connector penetrating said endcap thereinto.

8. A pressure compensated transducer for transmitting and receiving sound as recited in claim 7, wherein said support housing is fabricated from an electrically conductive material, said housing electrically connected to the piezoelectric element configuration circuit.

9. A pressure-compensated transducer for transmitting and receiving sound as recited in claim 8, further comprising a plurality of said pressure-compensated transducers, said plurality of transducers defining a sound transducer array, said array physically and electrically connected in a configuration selected from a group consisting of a line array, a planar array and a volumetric array.

10. A pressure compensated transducer for transmitting and receiving sound, said transducer comprising:
  a rigid, impermeable support housing, said housing having an outer surface, an inner surface, a first rim bordering a first opening, a second rim bordering a second opening, said housing having a first connecting means for a plurality of electrically conducting leads penetrating thereinto;
  a pressure compensating mensurational duct, having an inner orifice and an outer orifice, said duct piercing said housing, said inner orifice abutting said inner surface and said outer orifice abutting said outer surface, said mensurational duct having mensural parameters calculated and determined prior to fabrication thereof;
  a first piezoelectric element, affixed to a concomitant first flexural metal plate by means of an electrically conductive bonding agent, said first plate having a first peripheral edge, said first peripheral edge impermeably affixed and sealed to said first rim of said housing;
  a second piezoelectric element, affixed to a concomitant second flexural metal plate by means of an electrically conductive bonding agent, said second plate having a second peripheral edge, said second peripheral edge impermeably affixed and sealed to said second rim of said housing, said first piezoelectric element and said second piezoelectric element electrically connected to each other in a piezoelectric element configuration circuit, the piezoelectric element configuration circuit electrically connected to a plurality of electrically conducting leads, said conducting leads connecting to said first means and extending therefrom, for subsequently connecting the piezoelectric element configuration circuit to a sound signal conditioning system;
  a protective boot, fabricated from a compliant impermeable material, said boot having a boot outer wall, a boot inner wall, and a singular opening thereinto, said boot inner wall having a plurality of boot ribs molded thereinto, said boot and said ribs receiving said housing and securely maintaining position of said housing within said boot; said boot further having an impermeable, rigid end cap, having an inner cap surface and an outer cap surface, said cap having a second electrical connecting means penetrating thereinto, said second connecting means receiving said plurality of electrical conducting leads connected to said first connecting means and extending therefrom, said second connecting means having said leads extending therefrom, said connecting leads connected from said second connecting means to the sound signal conditioning system, said end cap received into and securely affixed against said inner wall of said boot with a sealing band;
  an inner reservoir, defined by the void bounded by said inner surface, said first rim and said second rim of said housing; and
  an outer reservoir, totally surrounding said housing, defined by the void between said outer surface of said housing, said boot inner wall of said boot, and said inner cap surface of said end cap, said inner reservoir and said outer reservoir completely filled with a pressure compensating fluid, said inner orifice of said mensurational duct proximate to said inner reservoir and said outer orifice of said duct proximate to said outer reservoir, for communicating flow of the pressure compensating fluid between said outer reservoir and said inner reservoir, said boot retaining and protecting the pressure compensating fluid from escaping into the external operating environment and preventing contamination of the pressure compensating fluid from the external operating environment, for providing pressure compensation and equalization of ambient pressure variations on each surface of said first and second piezoelectric elements.

11. A pressure compensated transducer for transmitting and receiving sound, as recited in claim 10, wherein said support housing is tubiform, having a first open end corresponding to said first opening and a second open end corresponding to said second opening, said open ends opposing each other; said first piezoelectric element and said concomitant first flexural metal plate are disks; and said second piezoelectric element and said concomitant second flexural metal plate are disks, said flexural disks and said piezoelectric elements affixed thereto are affixed to said rims of said support housing such that said piezoelectric elements face said inner reservoir.

12. A pressure compensated transducer for transmitting and receiving sound, as recited in claim 11, wherein said first connecting means comprises a first impermeable feedthrough electrical connector penetrating said support housing for said plurality of conducting leads.

13. A pressure compensated transducer for transmitting and receiving sound, as recited in claim 12, wherein said second connecting means comprises a second impermeable feedthrough electrical connector penetrating said end cap for said plurality of conducting leads.

14. A pressure compensated transducer for transmitting and receiving sound, as recited in claim 13, wherein said support housing is fabricated from an electrically conductive material, said housing electrically connected to the piezoelectric element configuration circuit.

15. A pressure compensated transducer for transmitting and receiving sound, as recited in claim 14, wherein said boot is tubiform, said boot having a singular opening at one end of the tubiform.

16. A pressure-compensated transducer for transmitting and receiving sound as recited in claim 15, wherein said transducer is replicated multiply to produce a plurality of pressure compensated transducer s, said plurality of transducers defining a sound transducer array, said array physically and electrically connected in a configuration selected from a group consisting of a line array, a planar array and a volumetric array.

17. A pressure-compensated transducer as recited in claim 15, wherein said second piezoelectric element and said concomitant second flexural metal disk are replaced by a rigid impermeable plate affixed to said second rim of said support housing.

18. A pressure compensated transducer for transmitting and receiving sound, said transducer comprising:
  a rigid, tubiform support housing, made of an impermeable, electrically-conductive material, said housing having an outer surface, an inner surface, a first rim bordering a first opening at one end of said tubiform housing, a second rim bordering a second opening at other, remaining end of said housing, said housing having a first impermeable feedthrough electrical connector penetrating thereinto;

a pressure compensating mensurational duct, having an inner orifice and an outer orifice, said duct piercing said housing, said inner orifice abutting said inner surface of said housing and said outer orifice abutting said outer surface of said housing, said mensurational duct having duct mensural parameters, including length, circumference, and orifice area, calculated and derived prior to fabrication thereof;

a first piezoelectric element, securely affixed to a concomitant first flexural metal disk by means of an electrically conductive bonding agent, said first disk having a first peripheral edge, said first peripheral edge impermeably securely affixed and sealed to said first rim of said housing, said first piezoelectric element facing interior of said housing toward said second rim;

a second piezoelectric element, securely affixed to a concomitant second flexural metal disk by means of an electrically conductive bonding agent, said second disk having a second peripheral edge, said second peripheral edge impermeably securely affixed and sealed to said second rim of said housing, said second piezoelectric element facing interior of said housing toward said first rim, said first piezoelectric element and said second piezoelectric element electrically connected to each other in a piezoelectric element configuration circuit, the element configuration circuit electrically connected to a plurality of electrically conducting leads, said conducting leads connecting to said first feedthrough connector and extending therefrom, for subsequently connecting the piezoelectric element configuration circuit to a sound signal conditioning system;

a protective tubiform boot, fabricated from a compliant impermeable material, said boot having a boot outer wall, a boot inner wall, and a singular opening thereinto, said boot inner wall having a plurality of boot ribs molded thereinto, said boot and said ribs receiving said housing and securely maintaining position of said housing within said boot, said boot further including an impermeable, rigid end cap, said cap having an inner cap surface and an outer cap surface, said cap having a second electrical connector penetrating thereinto, said second connector receiving said plurality of electrical conducting leads connected to said first connector and extending therefrom, said second connector having said leads extending therefrom, said connecting leads connected from said second connector to the sound signal conditioning system, said end cap received into said singular opening and securely affixed against said inner wall of said boot with a sealing band, said sealing band sealing the interior of said boot from the environment external to said pressure compensating transducer;

an inner reservoir, defined by the void bounded by said inner surface, said first rim, and said second rim of said housing, said inner reservoir having physical properties including an inner reservoir volume; and an outer reservoir, defined by the void between said outer surface of said housing, said boot inner wall of said boot, and said inner cap surface of said end cap, said outer reservoir having physical properties including an outer reservoir volume, said inner reservoir and said outer reservoir completely filled with a pressure compensating fluid, said sealing band and said end cap retaining the fluid within said boot, preventing contamination of the compensating fluid from and preventing loss of the compensating fluid to the environment external to said transducer, the compensating fluid having fluid physical properties including viscosity and bulk modulus, said mensurational duct fabricated according to said duct mensural parameters derived from calculations involving said inner reservoir volume, the fluid physical properties of the compensating fluid, and expected temperature of the external environment of said pressure compensated sound transducer, said inner orifice of said mensurational duct proximate to said inner reservoir and said outer orifice of said duct proximate to said outer reservoir, for communicating flow of the pressure compensating fluid between said outer reservoir and said inner reservoir, for providing pressure compensation and equalization of ambient pressure variations on each surface of said first and second piezoelectric elements.

19. A pressure-compensated transducer for transmitting and receiving sound as recited in claim 18, wherein said pressure-compensated transducer is a component of an assemblage of like sound transducers, the assemblage defining a sound transducer array, the array electrically connected in a configuration selected from a group consisting of a line array, a planar array and a volumetric array.

20. A pressure-compensated transducer for transmitting and receiving sound as recited in claim 18, wherein said second piezoelectric element and said concomitant second flexural metal disk is replaced with a rigid, impermeable disk, the edge of said rigid, impermeable disk impermeably, securely affixed and sealed to said second rim of said housing.

* * * * *